United States Patent [19]
Shortt

[11] Patent Number: 5,528,366
[45] Date of Patent: Jun. 18, 1996

US005528366A

[54] PRECISION DETERMINATION FOR MOLECULAR WEIGHTS

[75] Inventor: David W. Shortt, Santa Barbara, Calif.

[73] Assignee: Wyatt Technology Corporation, Santa Barbara, Calif.

[21] Appl. No.: 326,628

[22] Filed: Oct. 20, 1994

Related U.S. Application Data

[63] Continuation-in-part of Ser. No. 188,268, Jan. 27, 1994, abandoned.

[51] Int. Cl.⁶ .................................................. G01N 21/17
[52] U.S. Cl. .................................................. 356/344
[58] Field of Search .................................................. 356/344

[56] References Cited

U.S. PATENT DOCUMENTS 4,875,169 10/1989 Synovec et al. .................... 364/497

OTHER PUBLICATIONS

Papazian et al. "Long and Short Range Precision in HPSEC," Journal of Liquid Chromatography, 13(1), 25–49 (1990).

Primary Examiner—Richard A. Rosenberger
Attorney, Agent, or Firm—Philip J. Wyatt

[57] ABSTRACT

This invention describes a method by which the precision of the reported molecular weights and radii of chromatographically separated molecules may be estimated. By suitably analyzing both the baseline and peak regions of a chromatogram, one may determine standard deviations of the signals from the various chromatographic detectors used in the analysis. This procedure yields standard deviations of the calculated values of molecular weight and root mean square radius of the separated molecules, as well as standard deviations of the calculated moments of the distribution of molecules. These standard deviations provide an estimate of the precision of the measurements.

15 Claims, 2 Drawing Sheets

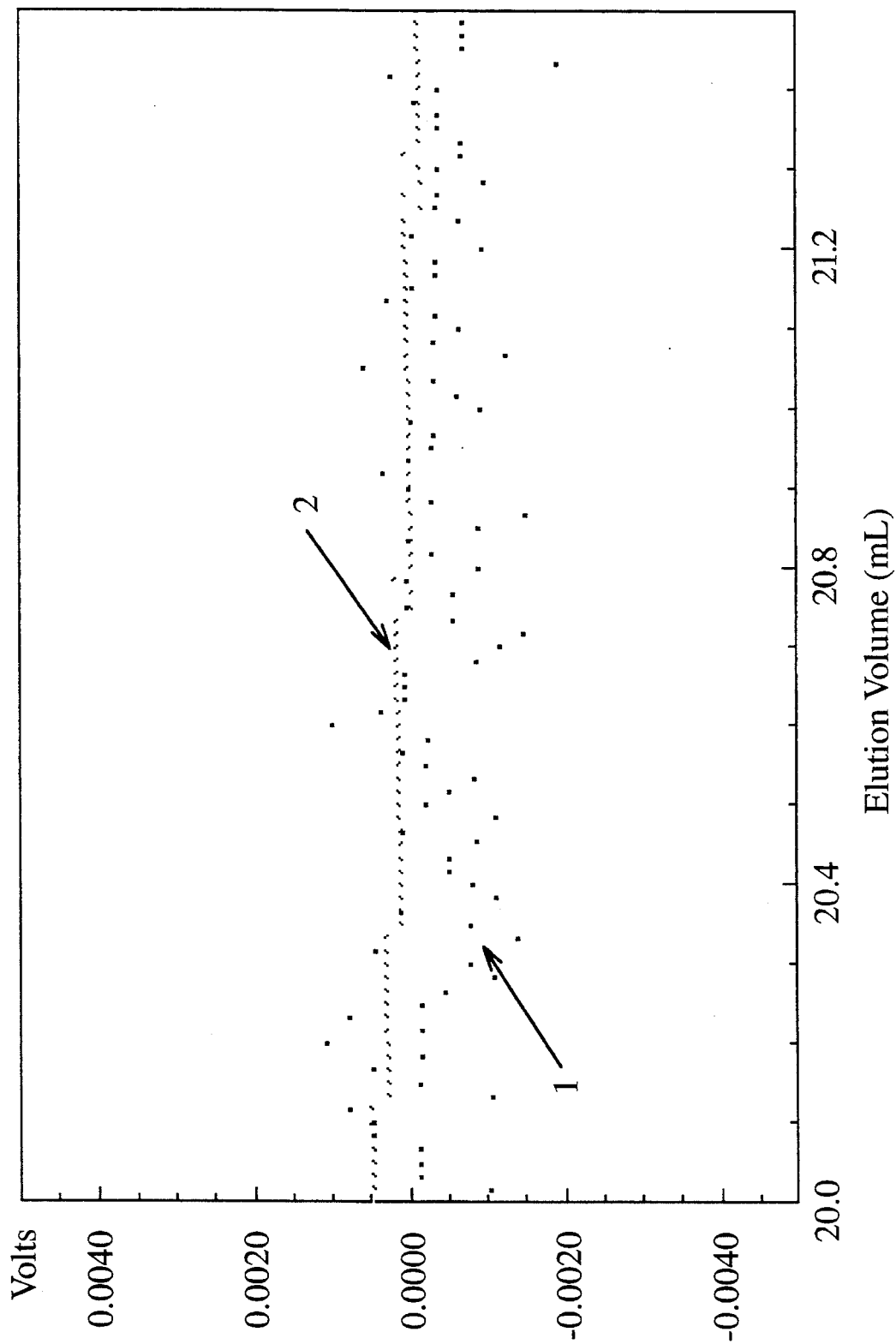

PRECISION DETERMINATION FOR MOLECULAR WEIGHTS

This application is a continuation-in-part of Ser. No. 188,268, filed Jan. 27, 1994, now abandoned.

REFERENCES

L. A. Papazian and T. D. Murphy, "Long and short range precision in HPSEC," J. Liq. Chrom. 13(1), 25–49 (1990).

W. H. Press, B. P. Flannery, S. A. Teukolsky, and W. T. Vetterling, *Numerical Recipes in C,* (Cambridge University Press, Cambridge, 1988).

John R. Taylor, *An Introduction to Error Analysis,* (University Science Books, Mill Valley, 1982).

B. H. Zimm, "The scattering of light and the radial distribution function of high polymer solutions," J. Chem. Phys. 16, 1093–1099 (1948).

B. H. Zimm and W. H. Stockmayer, "The dimensions of chain molecules containing branches and rings," J. Chem. Phys. 17, 1301–1314 (1949).

DEFINITIONS

This invention describes a method by which the precision of the reported molecular weights of chromatographically separated molecules may be estimated. Some of the terminology unique to the field of chromatography is as follows:

The term "baseline" refers to the relatively flat regions of a chromatogram before and after an eluting peak.

The term "calibration curve" refers to the curve traditionally needed to calibrate a chromatography system, usually a plot of the logarithm of molecular weight vs. elution volume or elution time.

The term "chromatogram" refers to a graph of a detector's signal vs. elution volume or elution time.

The term "chromatograph" refers to a system which performs a separation based on a physical property of the sample.

The term "chromatography" refers to the separation of a sample containing a mixture of materials by a technique sensitive to some physical property of the materials. For example, size exclusion chromatography, SEC, separates molecules by their hydrodynamic size.

The term "elution volume" refers to the volume of solvent which has passed through the detector(s) since the sample was injected. The elution volume is equal to the product of the elution time and the solvent flow rate.

The term "mobile phase" refers to the solvent which flows through the chromatography system.

A molecule's "molecular weight" is the mass of the molecule, measured in grams per mole. For example, the molecular weight of a toluene molecule is approximately 92 g/mol.

The term "polydispersity" refers to the ratio of the weight-average molecular weight to the number-average molecular weight. The polydispersity is always greater than or equal to unity. A value of unity indicates a monodisperse distribution (i.e., equal weight and number averages). Polymers can be characterized from narrow to broad, depending on whether the polydispersity is close to unity or far from it, respectively.

The term "Rayleigh ratio" refers to a quantity proportional to the amount of light scattered by a sample solution at a particular angle. The term "excess Rayleigh ratio" refers to that part of the scattered light due only to the solute molecules, not including the scattering due to the mobile phase.

The term "rms radius" refers to the root mean square radius of a molecule. This is the square root of the mean square radius, which is the mass-weighted average square distance of each molecular segment from the molecule's center of mass.

The term "slice" refers to the data collected from all detectors (light scattering and concentration) at a moment in time. Data are usually collected at equal time intervals.

BACKGROUND

Liquid chromatography, and in particular high performance size exclusion chromatography, HPSEC, is a useful tool for the characterization of polymers. Typically, samples are prepared and injected into a chromatograph where they are pumped through columns that separate the molecules. In the case of HPSEC, molecules are separated by their hydrodynamic size; smaller molecules tend to remain longer in the interstices of the columns and therefore elute at later times than larger molecules. Historically, the chromatograph with its separating columns and concentration sensitive detector was calibrated by using nearly monodisperse polymeric standards spanning a broad range of molecular weight, MW, that bracketed those expected for the unknown samples being processed and analyzed. The MWs present in the unknown sample were thus derived from a measurement of the time required for each separated fraction of sample to pass through the chromatograph relative to the corresponding times for the narrow calibration standards. Since the mobile phase is generally pumped through the chromatograph at a constant rate, the time of passage of a sample through the system may be represented equivalently in terms of the cumulative volume of fluid eluted, i.e. the so-called elution volume.

Calibration-dependent techniques contain a number of sources of error, both random and systematic. Random errors are caused by variations in chromatographic conditions from run to run and differences in baseline and peak settings. Systematic errors arise from several causes. First, the calibration curve itself is generally only an approximation to the relationship between the logarithm of the MW and the elution volume. The MW values of the standards contain uncertainties, many having been obtained from other calibration curve-based measurements. Second, the conformational differences that may exist between the calibration standards and the unknowns, which will result in elution times at considerable variance with those expected to correspond to the unknown's true MW, will exacerbate further these systematic errors and make them quite difficult to detect. Finally, since some time interval inevitably elapses between the calibration and the measurement, drifts in system parameters such as flow rate and temperature become important.

Nevertheless, even if results generated from standards were inaccurate, the reproducibility of such measurements still provided an important basis for their utility. Indeed, as pointed out by Papazian and Murphy in their 1990 article in the Journal of Liquid Chromatography, repeated analyses of the same samples over many months and even years of measurements are used to estimate the relative uncertainties of the results presented. These uncertainties could be used to monitor the stability of the calibration procedures as well as the degradation of the columns themselves. But virtually every measurement of an HPSEC separation reported in the literature presents MWs without any estimate of the precision of the reported results. Software packages which process the collected data often report results to six or more significant figures with complete disregard for the fact that such accuracy is impossible.

With the advent of in-line light scattering detectors, the need to calibrate was no longer required, since a light scattering detector combined with a concentration detector permitted the determination of MWs and sizes, and their distributions, on an absolute basis. The intrinsic inaccuracies of results based on the calibration standards themselves, which were rarely of the same configuration as the unknown being analyzed, no longer affected the final results. This eliminates much of the systematic error discussed above, but the random errors still remain. In-line light scattering measurements, especially those including many simultaneous angles such as performed by the system of light scattering detectors manufactured by Wyatt Technology Corporation under the registered trade name DAWN, generally include so many data that one is naturally challenged to ask if the data are sufficient to calculate directly a measure of the precision of the results based on a single chromatographic run. Despite the fact that such amounts of collected data have been available for some time, it has heretofore gone unrecognized that estimates of precision were possible. During my study of many of these data collections, it has become apparent to me how these critical numbers could be generated.

Under normal circumstances, each detector in a chromatograph gives a signal which contains a peak, or several peaks, rising out of a flat baseline. In FIG. 1 appears the signal from one of the light scattering detectors along with the concentration-sensitive detector. In order to calculate a MW and rms radius for each slice, one must compute the ratio of the light scattering signal for each angle to the concentration signal, and fit these data to a model as a function of angle. When appropriate scaling is chosen, the value of the fit at zero angle, called the "intercept", is related to the MW, and the ratio of slope to intercept at zero angle is related to the mean square radius. These techniques have been thoroughly developed in the literature, for example in the articles by Zimm which appeared in the Journal of Chemical Physics beginning in 1948.

More specifically, consider the molecules, having been separated by the chromatograph, which elute at a particular volume corresponding to a slice i. These molecules are dissolved at a concentration $c_i$ which may be measured by the concentration sensitive detector. In addition, the molecules scatter light which can be measured by the light scattering detector at a set of angles $\theta_j$. The light scattered from the molecules is described by excess Rayleigh ratios $R(\theta_j)$. At suitably low concentrations, these measured excess Rayleigh ratios are related to the weight average molecular weight $M_i$, and the second virial coefficient $A_2$ by the relation $$\frac{R(\theta_j)}{K^* c_i} = M_i P_i(\theta_j) - 2 A_2 M_i^2 P_i^2(\theta_j) c_i. \quad (1)$$

Here, the quantity $K^*$ is an optical parameter defined by $$K^* 4\pi^2 n_0^2 (dn/dc)^2 \lambda_0^{-4} N_A^{-1} \quad (2)$$

where $n_0$ is the solvent refractive index, $dn/dc$ is the specific refractive index increment of the solution, $\lambda_0$ is the vacuum wavelength of the incident light, and $N_A$ is Avogadro's number. The quantity $P_i(\theta)$ is called the scattering function or form factor for slice i and may always be written as a polynomial in $\sin^2(\theta/2)$:

$$P_i(\theta) = 1 - \frac{16\pi^2 n_0^2}{3\lambda_0^2} <r^2>_i \sin^2(\theta/2) + \alpha_2 \sin^4(\theta/2) + \ldots \quad (3)$$

where $<r^2>_i$ is the mean square radius of the scattering molecules averaged over the distribution present at slice i. If the molecules are known to be of a particular form, the expression for $P_i(\theta)$ can be written in closed form. For example, if the molecules obey the random coil approximation, common for many types of polymer molecules, the scattering function can be written $$P_i(\theta) = \frac{2}{x_i^2} [\exp(-x_i) - 1 + x_i] \quad (4)$$

where $$x_i = \frac{48\pi^2}{3\lambda^2} <r^2>_i \sin^2(\theta/2). \quad (5)$$

The calculations may also be performed using a reciprocal version of Eq. (1), namely $$\frac{K^* c_i}{R(\theta_j)} = \frac{1}{M_i P_i(\theta_j)} + 2 A_2 c_i. \quad (6)$$

All the same analysis techniques described below apply to both Eqs. (1) and (6).

Light scattering detectors at very low and very high angles are sometimes unusable due to high noise levels from particulates or stray light. Even when usable, these detectors often have more noise than mid-range angles. This noise shows up in the baseline as well as in the peaks. The noise level of the concentration detector is typically, but not always, less than for the light scattering detectors.

Ideally, It would be very desirable to be able to calculate the uncertainty in the MW and rms radius for each slice from which comparable uncertainties for an entire peak could be generated using standard methods of error propagation. This would provide a statistical estimate of the typical variation one would expect to see from repeated measurements of the same sample. Such a calculation could save considerable time as well as provide an independent measure of the precision of the measurement. Unfortunately, measurement of the uncertainties associated with a single slice would require that repeated measurements be made as each slice elutes. Such measurements would have to be made over long enough periods of time to permit the collection of the plurality of values from which their corresponding standard deviations could be calculated, following standard statistical procedures. Yet the fundamental concept of making a chromatographic separation relies upon the requirement that the eluting sample be divided into slices, each one of which occurs over a time frame very short compared to that required for the whole sample. Measurement of a single slice cannot be frozen in time in order to quantify its fluctuation.

Despite these apparent contradictions, my invention shows clearly how the precision of determinations using chromatographic separations may now be estimated quite easily. Although the method has focused almost entirely upon analyses of data collected in the preferred embodiment of an in-line multi-angle light scattering detector, my invention may certainly be practiced by those skilled in the art for other types of light scattering detector systems incorporating one, two, three, or more angles for their measurements, as well as for measurements and precision determinations of viscometric quantities.

BRIEF DESCRIPTION OF THE FIGURES

FIG. 2 shows an enlarged view of the following baseline region 4 of FIG. 1 containing typical noise fluctuations.

BRIEF DESCRIPTION OF THE INVENTION

Figure 1:
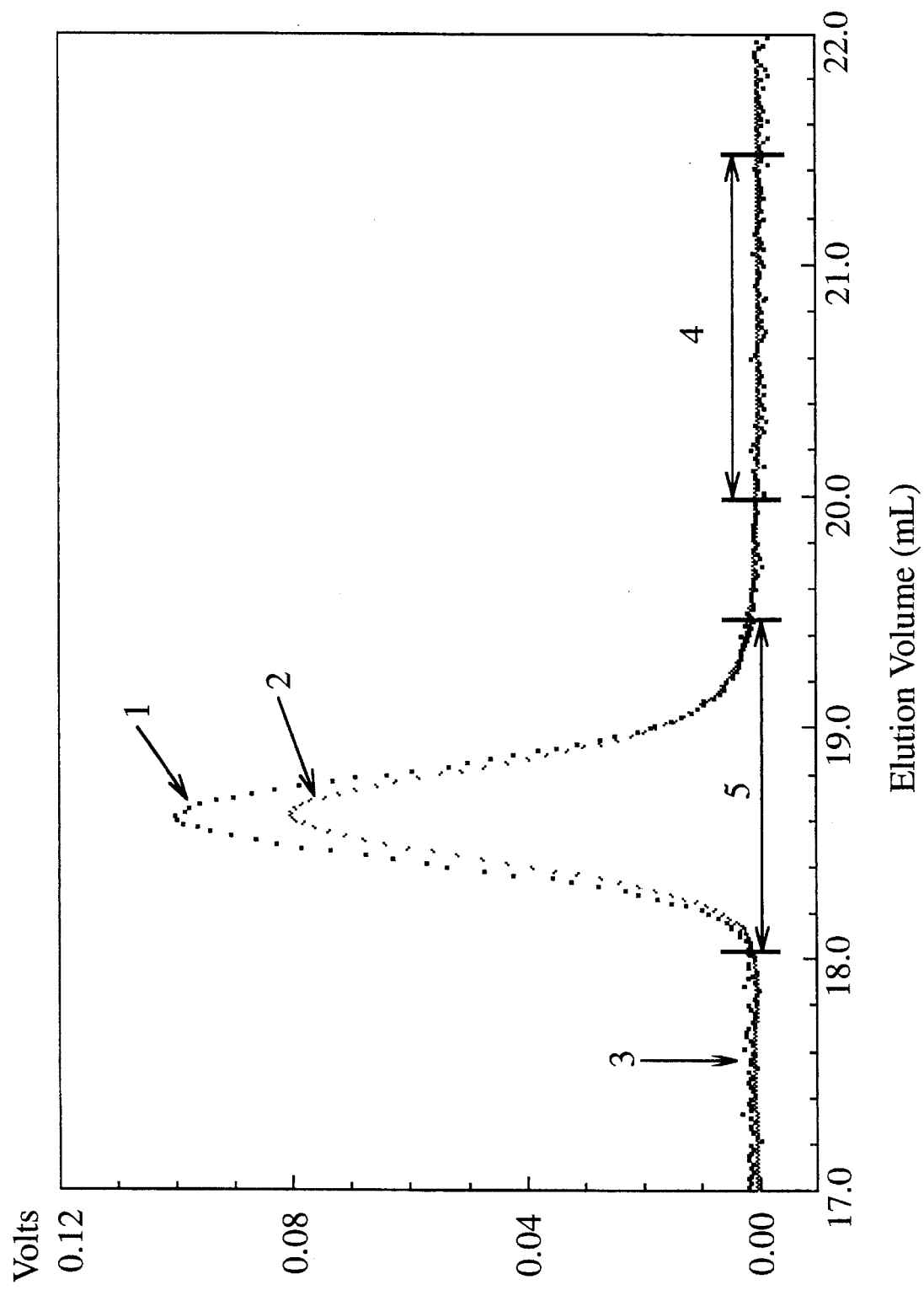
FIG. 1 shows typical chromatograms showing the light scattering signal at 90° with the concentration detector signal superimposed. Clearly visible are the leading and following baseline regions and the peak.

FIG. 1 shows a typical chromatogram contrasting the scattering of light at 90° 1 with the concentration sensitive refractive index detector signal 2. The sample was a narrow distribution standard of polystyrene having a MW of approximately 30,000 grams per mole. The mobile phase was toluene, and a total mass of 0.2 mg was injected before the columns in an injection volume of 100 μL. Two relatively flat baseline regions, 3 and 4, lie on either side of the peak region 5. The invention rests on these observations:

The calculations of molecular weight and size only use the peak region 5 where the signal is significantly greater than the baseline noise, as marked in FIG. 1. In other words, the baseline regions 3 and 4 contain no information about the MW and rms radius and are unaffected by the sample. The only factors contributing to the noise of the sample that would differ from those present in the mobile phase corresponding to the baseline regions 3 and 4 would be those aggregates and agglomerates introduced with the sample itself. Because of the separation processes associated with the sample's passage through the chromatographic column, this type of spurious debris will generally be separated from the sample itself and will not contribute to the chromatogram of the peak region.

Since the spurious contributions introduced with the sample have been removed by the column, the amount of noise present in the baseline regions 3 and 4 is a direct measure of that present in the peak region 5. The presence of the peaks neither adds to nor subtracts from this.

Suitable analysis of the baseline regions can yield standard deviations for each light scattering detector in the multi-angle instrument, as well as the standard deviation for the concentration detector. The baseline region 4 is shown at an expanded scale in FIG. 2. The 90° light scattering signal 1 shows clear evidence of noise fluctuations, while the refractive index signal 2 shows a slight drift and very little noise.

Applying these baseline standard deviations to the peak region 5 allows the calculation of standard deviations in the concentration, MW, and rms radius through the standard statistical procedure called propagation of errors. Thus the baseline regions 3 and 4, while providing no information about the values of MW and rms radius, do indeed contain information from which the standard deviation of the MW and rms radius may be determined.

If the statistical processes governing the noise obey certain reasonable assumptions, the standard deviations obtained for MW and rms radius can be taken as typical of the fluctuation that would occur over multiple runs of the same sample.

Thus by analyzing both the baseline regions 3 and 4 as well as the peak region 5, standard deviations in the calculated quantities can be obtained. Historically, the baseline regions 3 and 4 were only used to determine the baseline values to be subtracted from the data prior to analysis, and a drifting or noisy baseline indicated a problem with a detector or with the chromatograph itself. The statistical significance of the information inherent in the baseline noise has not been heretofore noted nor used in any statistical analyses.

My method, a detailed description of which appears below, has several important benefits including the following:

The method permits the calculation of the standard deviations in concentration, MW, and rms radius at each slice from a chromatographic elution using a multi-angle light scattering instrument and a concentration-sensitive detector. Were only a single LS detector available, then no rms radius value would be calculable, and the MW value could be erroneous. However, the precision of the MW result would still be calculable.

The method permits the calculation of the standard deviations in MW and rms radius averages for a range of slices defining a peak.

Noisy light scattering detectors are automatically identified, and their contribution to the calculated results is automatically reduced.

The method may be applied to any theoretical model of molecular structure, including but not limited to random coil, sphere, rigid rod, or simple polynomial of any degree.

The method may be applied also to the measurement and interpretation of in-line viscometric determinations.

DETAILED DESCRIPTION OF THE INVENTION

As discussed in the background section of this specification, the calculation of the precision of any derived molecular weight or size moment requires, by use of propagation of error procedures, that the standard deviations of the molecular weight and concentration be measured at each slice. The basic difficulty with this concept is that multiple measurements of the light scattering and concentration signals cannot be performed on the same slice since chromatographic separations are continually changing with time. The fluctuations in the signal at a particular slice will generally occur in a time frame much larger than the time within which data for a single slice are collected, so trying to make multiple measurements within the timeframe of a single slice would generally result in multiple measurements of the very same signal! If we needed multiple measurements on the same slice, we would have to perform multiple identical injections and require that the chromatograms did not change between runs. This procedure would demand stability and reproducibility probably unachievable in practice; it would be extremely difficult to know that the various slices overlapped correctly and that chromatographic conditions did not change. The paper by Papazian and Murphy describes how averages have been made historically, i.e. by relying upon data collected from multiple injections made over long periods of time. This procedure, however, can only be used to determine the precision of certain physical quantities. Thus for a particular polymer standard, various averages over the eluting peak (for example, the weight average molecular weight) may be determined by repetitive measurements. The sources of fluctuations of such derived averages can rarely be determined because of the near impossibility of maintaining constant chromatographic conditions over the time frames generally employed to collect the data. Slice-by-slice precision has never been previously determined by any method, yet if one really wanted to estimate the precision of an average molecular weight over the eluting peak of a particular polymer at the time of measurement, it could not be done since, until this invention, there has been no way to determine the fluctuations of the contributing slice data.

To illustrate these points, consider the weight average molecular weight of a chromatographic peak eluting over a period during which data at N slices were collected. The weight average molecular weight is defined as $$M_w = \sum_{i=1}^{N} c_i M_i / \sum_{i=1}^{N} c_i \qquad (7)$$

How can we determine the precision of $M_w$ itself without making multiple injections and repeated experiments, since the usual single measurement of each $c_i$ and $M_i$ has no a priori associated errors? Equation (8), below, shows how the associated standard deviation, $\sigma_{M_i}$ of each of the derived $M_i$ of Eq. (7) may be calculated following the usual methods for calculating the propagated errors. Traditionally, if we wanted to determine the precision of the molecular weight at a particular chromatographic slice i, the standard procedure would be to make M repeated measurements (j=1 to M) of the light scattering signals at that $i^{th}$ slice, $L_{ij}$, and of the concentration signals, $c_{ij}$, at that same slice. From these multiple measurements, we would first calculate the average light scattering signal $L_{avg_i}$ and its standard deviation $\sigma_{L_i}$ as well as a similar concentration average $c_{avg_i}$ and its associated standard deviation $\sigma_{c_i}$. From the ratio $L_{avg_i}/c_{avg_i}$ of these average values we would calculate the molecular weight $M_i$ for that $i^{th}$ slice. The standard deviation of the molecular weight for that $i^{th}$ slice would be calculated using standard propagation of error algorithms to yield $$\sigma_{M_i} = M_i \left( \frac{\sigma_{L_i}^2}{L_{avg_i}^2} + \frac{\sigma_{c_i}^2}{c_{avg_i}^2} \right)^{1/2} \qquad (8)$$

This result combined with each standard deviation $\sigma_{c_i}$ of the concentrations $c_{avg_i}$, the standard deviation of the weight average molecular weight $M_w$ of Eq. (7) may be calculated using standard propagation of error algorithms.

From an experimental point of view, however, the above procedure has always appeared impossible because there has been no way known to determine the standard deviations of the individual contributing elements at each slice. My invention discloses a method for estimating the standard deviation of each detected variable for all of the physical quantities measured at each slice without having to perform effectively impossible replicate experiments. This would include various concentration detectors such as refractive index detectors, ultraviolet detectors and evaporative mass detectors as well as light scattering detectors and viscosity detectors. Once these standard deviations have been found, one can apply conventional error propagation algorithms to obtain precision estimates for all derived quantities. This is a significant achievement whose need has been long recognized yet whose implementation has, until now, remained elusive.

The key element of my invention is the realization that the fluctuations in the baseline region, which are relatively easy to measure, are equivalent to the fluctuations in repeated measurements of a single slice, which are very difficult to measure. This is because any dust, aggregate, and debris components of a sample injected into a chromatographic system will generally be separated from the molecular elements of the sample. These components will be excluded, for the most part, from that chromatographic region within which the major sample constituents will lie. On the other hand, if the mobile phase itself contains a distribution of such noise-causing elements, they will remain unresolved, elute continuously even after the columns, and contribute, therefore, to each slice of the separated sample in an equivalent manner. The baseline itself reflects all of these contributions that cause uncertainties in the determination of the corresponding measurements within the slices. In addition, the baseline reflects all the noise elements associated with detector drift and electronic noise. Thus the fluctuations in the baseline region are equivalent to the fluctuations in repeated measurements of a single slice. By careful measurement of the baseline regions, we may determine thereby the quantity of noise affecting each and every slice of the separated sample.

Application of my invention may be broken down into a series of steps. A description of each step follows.

1. The signal $R_i(\theta_j)$ from each light scattering detector, as well as the signal $c_i$ from the concentration detector, at a slice i, has an intrinsic noise level due to dust, short term drifts, particulates, etc. This is also true for an in-line viscosity detector, were it used. The noise will in general have different magnitudes for each detector. We must first determine the noise level, called the "standard deviation", of the signal from each light scattering detector. FIG. 1 shows the 90° light scattering signal 1 and the concentration signal 2. The chromatographic peak or peaks in region 5 may be almost any shape and are therefore unsuitable for finding the noise level. However, the baseline regions 3 and 4, away from the peaks, are relatively flat and are to be used to determine the standard deviations in detector signals. Typical noise fluctuations in the 90° light scattering signal 1 and concentration signal 2 may be seen in FIG. 2, which shows the baseline region 4 at an expanded scale. A baseline region can be selected by the analyst or determined by an appropriate computer algorithm. In any case, the baseline region for each detector is fit, using the method of least squares, to a suitable model. Since the data are relatively constant in these baseline regions, the fit should be excellent. Standard treatments of numerical analysis such as that in the text *Numerical Recipes* by Press et al. explain that the assumption of a good fit allows an estimate of the standard deviations for the data points to be obtained.

The preferred embodiment of a computer algorithm fits an initial fraction or region of the data to a suitable baseline model. One possible choice is to fit the first 10% of the data, or 100 data points, whichever is smaller, to a third degree polynomial. Then the process could be repeated for the last 10% of the data, or 100 data points, whichever is smaller. Fitting only these end regions of the data maximizes the probability that the regions will contain only baseline data and that the peak or peaks elute after the leading baseline region and before the following baseline region. Fitting both end regions and taking the smaller standard deviation makes the method insensitive to outlier points. Using a third degree polynomial allows the method to work even if some part of a peak is inadvertently included. Typically, a data set will contain 500–2000 points or more, so the method will usually use at least 50 points for these baseline fits. Thus the third degree polynomial will not fluctuate appreciably between data points. Limiting the number of fitted points to 100 keeps calculation times short. This automatic approach does not require intervention by the analyst but rather assumes that at least 10% or 100 points of baseline data are collected either before or after the sample peak regions.

It should be emphasized that although the specific choices of 10%, 100 data points, use of both end regions, and a third degree polynomial are reasonable, many other options are possible, including allowing the user to specify any or all of these parameters, and even including using a model other than polynomial to determine the standard deviations. Different choices might optimize the procedure for different experimental conditions, but all these possible choices are merely alternative embodiments of this invention.

This baseline fitting procedure is performed once for each detector in the light scattering instrument, and once for the concentration detector.

2. For each slice i in each peak, the preferred computer analysis will calculate the ratio $R_i(\theta_j)/K^*c_i$ of the light scattering signal to the concentration signal for each angle $\theta_j$. From the standard deviations in the excess Rayleigh ratios $R_i(\theta_j)$ and the concentration signal $c_i$, previously determined in Step 1, the standard statistical method of propagation of errors, as described in the reference by Taylor, is used to obtain standard deviations in the ratios $R_i(\theta_j)/K^*c_i$ for each angle. For example, if we have two quantities a and b along with their respective uncertainties $\sigma_a$ and $\sigma_b$, we may form the ratio a/b and its associated uncertainty $$\sigma_{a/b} = (a/b)\sqrt{\left(\frac{\sigma_a}{a}\right)^2 + \left(\frac{\sigma_b}{b}\right)^2} . \quad (9)$$

3. Next, the ratios $R_i(\theta_j)/K^*c_i$ for each angle are fit to an appropriate theoretical model of the expected light scattering using the standard deviations derived in Step 2. Standard numerical methods exist for fitting data to any model, even non-linear models, when standard deviations in the input data are known. Such methods are described in the aforementioned reference by Press et al. Given ordered pairs of data $(x_j, y_j)$, with uncertainties $\sigma_j$ in the $y_j$, and given a model $y(x)$, the deviation between the data and the model is calculated according to the method of least squares. A quantity $x^2$ called "chi-square" is calculated by the expression $$\chi^2 = \sum_j \frac{[y_j - y(x_j)]^2}{\sigma_j^2} \quad (10)$$

and is minimized by adjusting the various parameters in the model. If the model $y(x)$ is linear in its parameters, such as is the case if $y(x)$ is a polynomial in x, the minimization can be completed in one step. If the model is non-linear, iterative methods are used. In either case the result is a minimum value of $x^2$ along with the best-fit parameters and their uncertainties. In the present application, for a particular slice i, the input data consist of the ordered pairs [$\sin^2(\theta_j/2)$, $R_i(\theta_j)/K^*c_i$]. The model consists of the right side of Eq. (1) or Eq. (6) with an appropriate choice of $P(\theta_j)$. The numerical method minimizes the deviation between the data and the model by adjusting the model parameters, namely the molecular weight $M_i$ and the mean square radius $<r^2>_i$. When performing the fit for each slice, ordered pairs with large standard deviations are relatively less important than ones with small standard deviations. Thus noisy light scattering detectors are automatically weighted so that they are less important to the overall fit. The results are best-fit values for the MW and the mean square radius along with standard deviations in the MW and mean square radius. To obtain the rms radius, one takes the square root of the mean square radius.

4. If the data contain no systematic errors, the value of $x^2$ obtained in Step 3 will be approximately equal to the number of degrees of freedom, defined as the difference between the number of angular detectors used in the fit and the number of fitted parameters. On the other hand, if there are systematic errors in the light scattering data, or if the chosen model is inappropriate to the data, the chosen model will not describe the data as well as the calculated standard deviations suggest it should, and the value of $x^2$ will be larger than the number of degrees of freedom. The preferred computer analysis accounts for this by increasing all the light scattering standard deviations by the same factor for each angle, in order to force $x^2$ to be equal to the number of degrees of freedom. This effectively increases the standard deviations in the calculated MW and rms radius. It also makes the implicit assumption that the chosen model describes the data well. Steps 2 through 4 are performed for each slice in each peak.

5. Standard expressions exist for combining the concentration, MW, and mean square radius for each slice to obtain the various moments or weighted averages of the MW and mean square radius for each peak. Using the standard statistical technique of propagation of errors, the standard deviations obtained in Step 3 for each slice are used to compute the standard deviations in each of the moments. This step is performed once for each peak after all the slice data have been analyzed. Naturally, there may be other functional combinations of the slice results which may be required other than the mass and radius moments referred to above. The precision of any such functional combination of concentration, MW, and mean square radius values within a selected peak region may be calculated similarly.

The truly novel additional elements of my invention are Steps 1 and 4. Steps 2, 3, and 5 are simple applications of standard numerical analysis techniques to light scattering.

Although I have concentrated entirely upon the application of my method to measurements of chromatographically separated samples using light scattering combined with concentration measurement, my method may be applied equally well to other on-line measurement techniques, such as viscometry. In the case of viscometry, the viscometer produces a signal proportional to the specific viscosity of the solution. By forming the ratio of specific viscosity to concentration, the intrinsic viscosity of the sample may be determined. Obviously, my method may be applied to this technique to yield precision estimates for the values of intrinsic viscosity, as well as for values of MW and hydrodynamic molecular radius derived by reference to so-called universal calibration curves. Similarly, for other combinations of techniques, such as viscometry and light scattering, by applying my method to each of the contributing signals and deriving therefrom the corresponding calculated quantities and standard deviations, one may derive molecular weights and sizes whose precision may be similarly calculated.

As will be evident to those skilled in the arts of data analysis and chromatography, there are many obvious variations of the methods I have invented and described that do not depart from the fundamental elements that I have listed for its practice; all such variations are but obvious implementations of my invention described hereinbefore and are included by reference to my claims, which follow.

I claim:

1. A method for estimating the standard deviation of each detected signal associated with the measurement at each slice of a chromatographically separated sample comprising the steps of:

a) locating a baseline region removed in time from the chromatographic peak of said separated sample corresponding to each said detected signal;

b) assuming a functional dependence with time of each said detected signal within said located baseline region;

c) calculating the standard deviation, $\sigma_j$, of each said detected signal with respect to said assumed functional dependence with time within said located baseline region;

d) fitting said detected signal, $x_j$, in the eluting peak region of said separated sample to an appropriate theoretical model, $y(x_j)$, by minimizing the expression $$\chi^2 = \sum_j \frac{[y_j - y(x_j)]^2}{\sigma_j^2}$$

where said baseline calculated standard deviations, $\sigma_j$, are associated with each said detected signal, $x_j$, e) generating a corrected standard deviation for each said baseline generated standard deviation $\sigma_j$ whenever the value of $\chi^2$ is larger than the number of degrees of freedom of said theoretical model by multiplying each said baseline generated standard deviation by the same factor to produce a value of $\chi^2$ equal to said number of degrees of freedom; and f) setting the standard deviation of each said detected signal at each said slice within said chromatographic peak of said separated sample equal to said baseline generated standard deviation or said corrected standard deviation as said $\chi^2$ is less than or larger than said number of degrees of freedom, or greater than said number of degrees of freedom, respectively.

2. The method of claim 1 where said detected signal is the concentration signal as measured by an in-line concentration detector.

3. The method of claim 2 where said concentration detector is a refractive index detector.

4. The method of claim 2 where said concentration detector is a ultraviolet detector.

5. The method of claim 2 where said concentration detector is an evaporative mass detector.

6. The method of claim 1 where said detected signal is the excess Rayleigh ratio, $R(\theta)$, at or about the scattering angle $\theta$ as measured by an in-line light scattering detector.

7. The method of claim 6 where said appropriate theoretical model is a random coil.

8. The method of claim 6 where said appropriate theoretical model is a polynomial in $\sin^2(\theta/2)$.

9. The method of claim 1 where said detected signal is the viscosity as measured by an in-line viscometer.

10. The method of claim 1 where said functional dependence with time of said detected signal within said located baseline region is a polynomial.

11. The method of claim 10 where said polynomial is of order zero.

12. The method of claim 10 where said polynomial is of order three.

13. The method of claim 1 where said baseline region is comprised of at least 10% of the baseline collected either before or after said chromatographic peak region of said separated sample.

14. The method of claim 1 where said baseline region is comprised of two parts: one baseline region before said sample peak region and one following it, with both parts analysed separately to yield two separate baseline standard deviations, the smallest of which is set equal to said baseline standard deviation of said detected signal at each said slice within said chromatographic peak of said separated sample.

15. A method for estimating the precision of a physical quantity derived from a set of detected signals obtained during a chromatographic separation comprising the steps of a) selecting an appropriate theoretical model describing the relation between the detected signals and said physical quantity;

b) attributing a corrected standard deviation to each said detected signal following the method of claim 1;

c) calculating the estimated precision of each said physical quantity derived from said set of detected signals by applying the standard statistical technique of propagation of error using said corrected standard deviations associated with each said detected signal.

* * * * *